United States Patent [19]

Elliott et al.

[11] Patent Number: 4,954,532
[45] Date of Patent: Sep. 4, 1990

[54] COSMETIC FORMULATON
[75] Inventors: Thomas J. Elliott, London; Susan Dutton, Northolt, both of England
[73] Assignee: Beecham Group p.l.c., England
[21] Appl. No.: 696,269
[22] Filed: Jan. 30, 1985
[30] Foreign Application Priority Data Feb. 1, 1984 [GB] United Kingdom ................. 8402637

[51] Int. Cl.$^5$ ....................... A61K 7/075; A61K 7/48; A61K 47/00
[52] U.S. Cl. ....................................... 514/846; 424/70; 514/847; 514/861; 514/864; 514/880; 514/881; 514/938; 514/939; 514/944
[58] Field of Search .......................... 514/847, 63, 846; 424/70

[56] References Cited
U.S. PATENT DOCUMENTS 4,000,317 12/1976 Menda et al. .......................... 424/69
4,071,374 1/1978 Minton ................................. 514/847

FOREIGN PATENT DOCUMENTS

| Number | Date | Country | Class |
|---|---|---|---|
| 0018137 | 3/1980 | European Pat. Off. | 424/68 |
| 0054701 | 6/1982 | European Pat. Off. | 514/63 |
| 2642032 | 3/1978 | Fed. Rep. of Germany | 514/63 |
| 2823595 | 12/1978 | Fed. Rep. of Germany | 514/63 |
| 56-68604 | 4/1981 | Japan | 424/63 |
| 0112314 | 7/1982 | Japan | 514/63 |
| 336019 | 8/1970 | U.S.S.R. | 514/63 |
| 1494656 | 3/1977 | United Kingdom | 424/70 |
| 2027341 | 2/1980 | United Kingdom | 424/63 |
| 2113116 | 8/1983 | United Kingdom | 424/70 |

*Primary Examiner*—Dale R. Ore
*Attorney, Agent, or Firm*—Jacobs & Jacobs

[57] ABSTRACT

A degreasing or moisturizing composition contains silanized silica gel, a humectant such as glycerine, and an inert carrier. The composition is used to treat sebhorreic conditions without causing dry skin.

5 Claims, No Drawings

COSMETIC FORMULATON

The present invention relates to the use of silanised adsorbents in particular antiseborrheic compositions.

Silanised silica gel is a known adsorbent and may be produced either by (a) treating fine particles of silica gel with a reactive silane thereby replacing many of the hydroxy groups with substituted siloxy groups, or (b) polymerising a suitable siloxane monomer in the presence of fine particles of silica gel thereby coating the particles with a polysiloxane.

Reactive silanes useful in method (a) above include alkyl, aryl especially phenyl and aralkyl especially benzyl halosilanes and -silazanes and alkyl, aryl especially phenyl and aralkyl especially benzyl alkoxysilanes and -silazanes.

Particular examples of such silanes include dimethyl monochlorosilane dimethyl dichlorosilane trimethylchlorosilane hexamethyl disilazane trichloro-octadecylsilane Suitable siloxane monomers for use in method (b) above include hydrogen polysiloxane such as methyl hydrogen polysiloxane and alkyl, aryl and aralkyl cyclotetrasiloxanes, especially octamethylcyclotetrasiloxane. Polymerisation may be effected by heating or chemical catalysis.

Similar techniques may be applied to produce silanised alumina, calcium carbonate, hydroxyapatite, iron oxide, mica, talc and derivatives thereof including titanated mica and talc. Method (a) above is suitable for silanising adsorbents having free hydroxyl groups, method (b) may be applied to most finely divided solids to produce a silanised adsorbent.

As used herein the term silanised adsorbent refers to silanised silica gel, alumina, calcium carbonate, hydroxyapatite, iron oxide, mica and talc and derivatives thereof. Silanised adsorbents have particularly advantageous properties as adsorbents of sebum enabling treatment of seborrhea by removal of sebum from the skin surface and hair.

As used herein the terms 'seborrhea' and 'seberrheic conditions' refer to a range of conditions from simple cosmetic 'greasy' skin and hair to clinical seborrhea which is often associated with pimpling or acne including dry acne. In all cases of seborrhea a major contributory factor is excessive secretion of sebum which accumulates in and on the stratum corneum and hair and/or in sebaceous follicles. Some contribution to the abnormally high lipid accumulation comes from the lipids exuded from differenciating skin cells. The use of silanised adsorbents is effective in all seborrheic conditions.

It is believed that silanised adsorbents not only remove the surface lipids but also drain the sebum from the lipid reservoirs in the stratum corneum and sebaceous follicles. The latter effect is important since by draining the reservoirs of sebum the rate of regreasing of the skin surface may be reduced with commensurate improvement in the appearance of the skin.

Silanised adsorbents also have an instant cosmetic matting effect thereby immediately improving the appearance of greasy skin. As they do not adsorb water, they do not have a tendency to cake and they remain effective despite perspiration and high ambient humidity.

We have now found that particular formulations of silanised adsorbents can provide both a degreasing effect and, at the same time, a moisturising effect thus enabling the treatment of sebhorreic conditions without causing dry skin conditions.

Accordingly the present invention provides a degreasing or moisturising composition comprising an effective amount of a silanised adsorbent, an effective amount of a humectant moisturising agent and an inert carrier or diluent therefor.

Preferably the silanised adsorbent is silanised silica gel, suitably having a mean particle size of 0.1 to 20 $\times 10^{-6}$m, the 'particles' consisting of aggregates of very fine 'primary particles' of much smaller size.

Suitable humectant moisturising agents include sorbitol, propylene glycol, glycerine and 'Lubrajel'. ('Lubrajel' is a proprietary material comrising a clathrate formed by reacting sodium glycerate and an acrylic acid polymer). Preferred humectant moisturisers are glycerine and Lubrajel.

Suitably the composition comprises from 0.1 to 5% by weight of silanised adsorbent. With silanised silica gel, a white deposit may be left if the composition contains over about 2.5% by weight of the silanised silica gel and preferably this material is included at from about 0.25 to 2.5% by weight, more preferably at about 0.5% by weight. Suitably the composition comprises from 2.5 to 15% by weight of humectant moisturising agent, more preferably from about 5 to about 10% by weight.

The composition may also comprise optional accessory ingredients such as suspending agents, perfume, colouring and preserving agents, pigments, keratolytics, antibacterials and antimicrobial agents such as Irgasan or chlorhexidine.

Examples of suspending agents include polyacrylic acid, carbomers, hydroxyalkyl cellulose, Xanthan gum and magnesium aluminium silicate.

Preferably a lower alkanol such as isopropanol or ethanol is included in any of the aforementioned compositions at from 5 to 40% w/w, more preferably at about 10% w/w to impart astringency and a cooling effect. Ethanol is preferred.

The compositions may be presented as conventional cosmetic formulations such as aqueous lotions or aqueous emulsions. Particularly suitable presentations include a cleansing lotion having an aqueous base and a treatment cream or lotion comprising respectively a water in solvent or solvent in water emulsion. In such emulsion presentations it is advantageous that the solvent should be volatile, thus after application the solvent evaporates rather than leaving an oily deposit on the skin. Suitable materials for use as solvents in these emulsions include isoparaffins, linear and cyclic polysiloxanes especially linear polydimethylsiloxanes and cyclomethicone. These may be included in the compositions at from 5 to 25% by weight, preferably at 10 to 20% by weight.

The diluent or carrier is usually water or a water/solvent emulsion. Suitably the compositions comprise 60 to 80% by weight of water.

The compositions are applied to the skin as required. The cleansing lotions mentioned above would typically be used twice a day whereas the treatment creams and lotions are suitably formulated as 'leave-on' products and would be applied once a day usually in the evening, then removed by washing in the morning.

The compositions of the invention may be prepared by admixing the ingredients at a temperature of from 0 to 100° C. and substantially atmospheric pressure, with optional heating within that temperature range to enable optimum mixing to occur.

The following Examples illustrate the invention but are not intended to limit the scope of the invention in any way.

EXAMPLE 1

| Cleansing lotion | % w/w |
|---|---|
| Silanised silica (Sipernat D10) | 0.5 |
| Ethanol | 10 |
| Suspending Agent | up to 1% |
| Lubrajel | 10 |
| Deionised water | to 100% |

This may be applied directly using a cotton-wool swab or may be impregnated into tissue-wipes.

EXAMPLE 2

| | | % w/w |
|---|---|---|
| (a) | Cyclomethicone/Dimethicone polyol | 10 |
| | Cyclomethicone | 10 |
| | Sodium Chloride | 2 |
| | Silanised silica | 0.5 |
| | Ethanol | 10 |
| | Lubrajel | 5 |
| | Deionised water | 62.5 |
| (b) | P.E.G. 22/Dodecyl glycol copolymer | 1 |
| | Cyclomethicone | 10 |
| | Silanised silica | 0.5 |
| | Ethanol | 10 |
| | Glycerine | 5 |
| | Deionised water | 73.5 |
| (c) | Glyceryl oleate | 1 |
| | Cyclomethicone | 20 |
| | Silanised silica | 0.5 |
| | Ethanol | 10 |
| | Lubrajel | 5 |

-continued

| | % w/w |
|---|---|
| Deionised water | 63.5 |

EXAMPLE 3

| | | % w/w |
|---|---|---|
| (a) | Stearic acid | 3 |
| | Cyclomethicone | 10 |
| | Ethanol | 10 |
| | Triethanolamine | 1 |
| | Silanised silica | 0.5 |
| | Deionised water | 70.5 |
| | Glycerine | 5 |
| (b) | Sorbitan stearate | 1.5 |
| | Polysorbate 60 | 2 |
| | Cyclomethicone | 10 |
| | Ethanol | 10 |
| | Silanised silica | 0.5 |
| | Deionised water | 71 |
| | Glycerine | 5 |
| (c) | Hydrogenated Tallow Glyceride Citrate | 1.5 |
| | Glyceryl palmitate lactate | 0.75 |
| | Cyclomethicone | 10 |
| | Ethanol | 10 |
| | Silanised silica | 0.5 |
| | Deionised water | 72.25 |
| | Glycerine | 5 |

We claim:

1. A degreasing or moisturizing composition, comprising from 0.1 to 5% by weight of a silanized silica gel, from 2.5 to 15% by weight of a humectant moisturizing agent, and an inert carrier or diluent therefor.

2. A composition according to claim 1, in which the silica gel has a mean particle size of from 0.1 to $20 \times 10^{-6}$m.

3. A composition according to claim 1, in which the humectant comprises sorbitol, propylene glycol, glycerine or a clathrate formed by reacting sodium glycerate and an acrylic acid polymer.

4. A composition according to claim 1, containing from 5 to 40% w/w of lower alkanol.

5. A method for degreasing or moisturising skin which comprises applying thereto an effective amount of a composition according to claim 1.

* * * * *